United States Patent [19]
Kast et al.

[11] Patent Number: 6,006,135
[45] Date of Patent: Dec. 21, 1999

[54] APPARATUS FOR INTERCONNECTING IMPLANTABLE ELECTRICAL LEADS AND MEDICAL DEVICE

[75] Inventors: John E. Kast, Hugo; Andrew J. Ries, Circle Pines; Thomas C. Bischoff, Minneapolis, all of Minn.

[73] Assignee: Medtronic, Inc., Minneapolis, Minn.

[21] Appl. No.: 08/938,736

[22] Filed: Sep. 26, 1997

[51] Int. Cl.[6] ........................................ A61N 1/375
[52] U.S. Cl. ............................ 607/37; 439/909; 439/652
[58] Field of Search .......................... 607/36–38, 115; 439/909, 651, 652

[56] References Cited

U.S. PATENT DOCUMENTS

| | | |
|---|---|---|
| 4,583,543 | 4/1986 | Peers-Trevarton . |
| 4,821,723 | 4/1989 | Baker, Jr. et al. . |
| 5,000,177 | 3/1991 | Hoffmann et al. . |
| 5,007,864 | 4/1991 | Stutz, Jr. . |
| 5,050,602 | 9/1991 | Osypka . |
| 5,060,649 | 10/1991 | Hocherl et al. . |
| 5,082,453 | 1/1992 | Stutz, Jr. . |
| 5,131,388 | 7/1992 | Pless et al. . |
| 5,144,946 | 9/1992 | Weinberg et al. . |
| 5,144,949 | 9/1992 | Olson . |
| 5,158,078 | 10/1992 | Benett et al. . |
| 5,199,428 | 4/1993 | Obel et al. . |
| 5,207,218 | 5/1993 | Carpentier et al. . |
| 5,312,453 | 5/1994 | Shelton et al. . |
| 5,314,430 | 5/1994 | Bardy . |
| 5,314,451 | 5/1994 | Mulier ........................................ 607/33 |
| 5,328,442 | 7/1994 | Levine . |
| 5,330,507 | 7/1994 | Schwartz . |
| 5,331,966 | 7/1994 | Bernett et al. . |
| 5,354,316 | 10/1994 | Keimel . |
| 5,374,279 | 12/1994 | Diffin, Jr. et al. . |
| 5,411,538 | 5/1995 | Lin ........................................ 607/33 |
| 5,443,065 | 8/1995 | Berghoff et al. ..................... 439/380 X |
| 5,545,186 | 8/1996 | Olson et al. . |

*Primary Examiner*—Jeffrey R. Jastrzab
*Attorney, Agent, or Firm*—Reed A. Duthler; Harold R. Patton

[57] ABSTRACT

A system for connecting electrical leads having connector assemblies carrying electrical connectors to an implantable electrical device having a device housing containing electrical circuitry, including a first connector module fixedly mounted to the device housing, with a first set of electrical connectors coupled to the circuitry within the device housing and a second connector module, with a second set of electrical connectors engageable with the first set of connectors and a second set of connectors electrically coupled to the second set of connectors and engageable with the connectors on the electrical leads and a mechanism for retaining the second module on an outer surface of the device housing adjacent the first module while the second set of connectors engages the first set of connectors. The first and second sets of connectors preferably engage one another as a result of movement of the second module in a first direction into engagement with the second connector module and the retaining mechanism preferably functions to engage and retain the second connector module on the outer surface of the device housing during movement of the second module in the first direction.

16 Claims, 15 Drawing Sheets

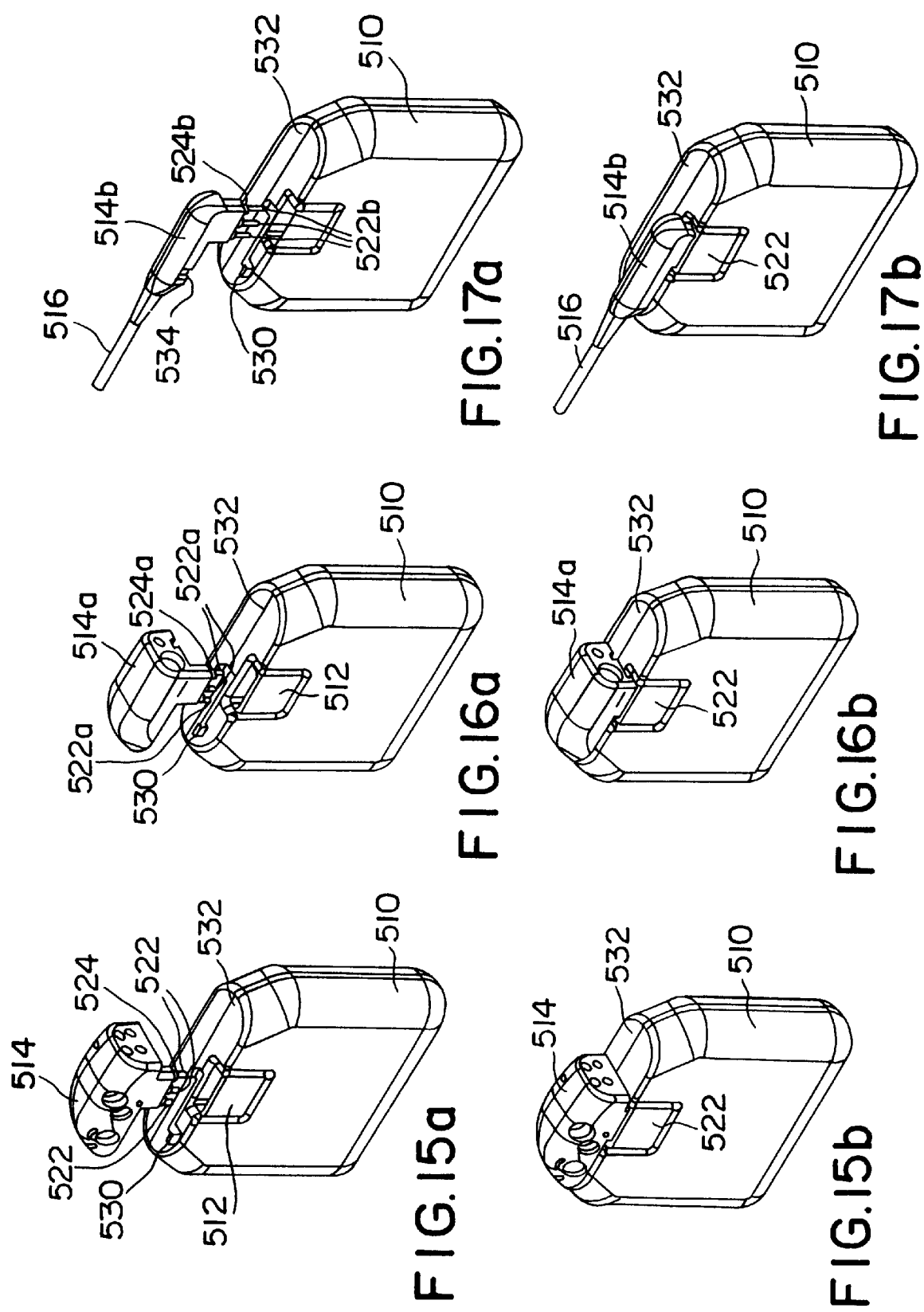

APPARATUS FOR INTERCONNECTING IMPLANTABLE ELECTRICAL LEADS AND MEDICAL DEVICE

BACKGROUND OF THE INVENTION

The present invention relates generally to mechanisms for interconnecting electrical leads and electrical medical devices, and more particularly to interconnecting implantable electrical leads and implantable medical electrical devices such as pacemakers, nerve stimulators, implantable defibrillators, implantable monitors and so forth.

As implantable electrical devices have increased in their complexity, there has been an increasing variety of electrical lead systems developed for use in conjunction with these devices. Nowhere is this more apparent than in the context of implantable cardioverter/defibrillators, which may include three, four, five, or more electrodes located on various numbers of implantable electrical leads. The leads themselves may carry one, two, three, or more electrodes, and may employ a variety of different electrical connector configurations and types. As a result, manufacturers of implantable cardioverter/defibrillators have had to produce their products with a variety of connector block configurations, capable of use with different lead systems. For example, Medtronic, Inc. presently manufactures implantable cardioverter/defibrillators with four basic connector designs, designated configurations "B", "C", "D", and "E". The "B" configuration includes three 6.5 mm connector bores for receiving high voltage electrical lead connectors of the type used to couple to cardioversion/defibrillation electrodes and one IS-1 compatible 3.2 mm in-line electrical connector bore for receiving an IS-1 electrical lead connector of the type generally used to couple to cardiac pacing and sensing electrodes. The "C" configuration includes a single 3.2 mm "DF-1" connector bore for receiving high voltage electrical lead connectors used to couple to cardioversion/defibrillation electrodes and a single IS-1 connector bore. The "D" configuration includes three DF-1 connector bores and one IS-1 connector bore. The "E" configuration includes two 6.5 mm connector bores and two 5 mm connector bores for receiving electrical lead connectors used to couple to individual cardiac pacing and sensing electrodes.

Traditionally, incompatibility between the configuration of the connector block and the connector assemblies on the implanted leads has been addressed by means of adapters. Typically, these adapters take the form of a relatively short lead which at one end has a connector assembly which may be inserted into one or more bores on the connector block on the implantable device and at the other end has one or more connector bores capable of receiving the connector assembly or assemblies on the electrical leads to be used with the device. These adapters are bulky and add substantially to the size of the pocket in which the device is to be implanted. In addition, they tend to require a number of additional steps to be performed by the physician in order to couple the leads to the implanted device, and are thus seen as undesirable generally. Such adapters are disclosed in U.S. Pat. No. 5,000,177, issued to Hoffmann, and U.S. Pat. No. 5,328,442, issued to Levine. Some adapters, such as disclosed in U.S. Pat. Nos. 5,050,602 issued to Osypka and 5,060,649 issued to Hocherl et al. even required removal of the connector assembly of the lead as part of the connection process. Another approach to resolving lead/device incompatibility problems is the up-sizing sleeve, as disclosed in U.S. Pat. No. 4,583,543, issued to Peers-Trevarton and U.S. Pat. No. 5,007,864, issued to Stutz Jr. However, up-sizing sleeves are usable only in cases in which the connector assembly of the lead is smaller than the connector bore, and only in some of these cases. While it would be preferable if a universal interconnection system could be developed for use in conjunction with implantable pacemakers, cardioverters and defibrillators, this goal remains elusive.

SUMMARY OF THE INVENTION

The present invention is directed toward a connection system for coupling an implantable device such as a pacemaker, cardioverter, defibrillator, nerve stimulator, muscle stimulator, implantable monitor or other device of the sort, to a set of one or more electrical leads and which addresses the lead/device incompatibility issues discussed above while avoiding at least some of the drawbacks associated with conventional adapters or converters. This goal is accomplished by means of a two-part connector block system, including a fixed connector module permanently mounted to the enclosure of the implanted device and a set of mountable connector modules which carry connector bores and associated electrical connectors having the desired configuration for each of a number of lead systems. For example, in the context of devices to be used in conjunction with Medtronic, Inc. defibrillators as described above, the mountable connector modules might include modules with connector bores and associated internal electrical connectors arranged in the same fashion as the above-described "B", "D", and "E" connector block assemblies.

The fixed connector module is mounted along a first edge of the enclosure of the implantable device, and includes a set of connector bores each containing an electrical connector coupled to the electronic circuitry within the device. The mountable connector modules are each provided with a set of connector bores with an associated first set of electrical connectors for coupling to electrical leads and are also provided with a second set of electrical connectors, coupled to the first set of connectors, and insertable into the connector bores of the fixed connector module to engage the connectors therein. The fixed connector module and/or the housing of the device also includes a mounting mechanism, working in conjunction with a cooperating mounting mechanism on the mountable connector modules to retain a mountable connector module on the housing of the device, along the first edge, adjacent the fixed connector module, with the second set of electrical connectors on the mountable connector module engaged with the connectors in the bores of the fixed connector module. When so assembled, the first set of connectors in the mountable connector module are coupled to the circuitry within the device and the fixed and mountable connector modules together approximate the external configuration of a traditional one-piece connector block. As such, the two-part connector block assembly adds relatively little to the overall size of the device, and thus does not require a substantially larger pocket for implantation.

The electrical connectors within the connector bores on the first component of the connector block are preferably of the "tool-less" type, so that the only step required in order to maintain electrical connection between the second set of connectors on the mountable module and the connectors in the fixed connector module is the insertion of the second set of connectors. The mechanism for retaining the mountable connector module along the first edge of the housing of the device is configured so that it attaches and locks the mountable connector module to the fixed connector module and the device concurrent with insertion of the second set of electrical connectors on the mountable module into the bores of the fixed connector module, also without requiring the use of a tool. As such, use of the two part connector block adds relatively little in the way of complexity to the implant process, as compared to a more conventional lead adapter or converter.

Finally, the interconnection mechanism for retaining the mountable connector module on the device is preferably reversible, so that in the event that a mountable connector block component with a different connector bore configuration is later needed. For example, in conjunction with a change in the lead set to be used with the device, a replacement of the mountable connector module can readily take place. Removal of the mountable connector module may be accomplished either manually by the physician or may require the use of a simple tool.

In a preferred embodiment of the invention, the fixed and mountable modules are provided with a sliding connector system including a rail mounted along the first edge of the device housing and a corresponding internal groove or grooves on the mountable module adapted to engage the rail. The rail and grooves are configured so that on sliding the mountable module along the groove, the second set of connectors on the mountable module are advanced into the bores on the fixed module. A mechanical lock in the form of a latch is also provided, so that concurrent with the second set of electrical connectors on the mountable module being fully inserted into the bores of the fixed module to engage the connectors therein, a mechanical interlock takes place preventing unintentional removal of the mountable module. The mountable module is then connected to the implantable lead set in precisely the manner employed in conjunction with prior art connector blocks. The system thus can be adapted to employ any of the various known mechanisms for connecting electrical leads and implantable devices.

BRIEF DESCRIPTION OF THE DRAWINGS

FIGS. 15a, 15b, 16a, 16b, 17a, and 17b are perspective views of a fourth embodiment of a two part connector block system according to the present invention.

DETAILED DESCRIPTION OF THE PREFERRED EMBODIMENTS

Figure 1:
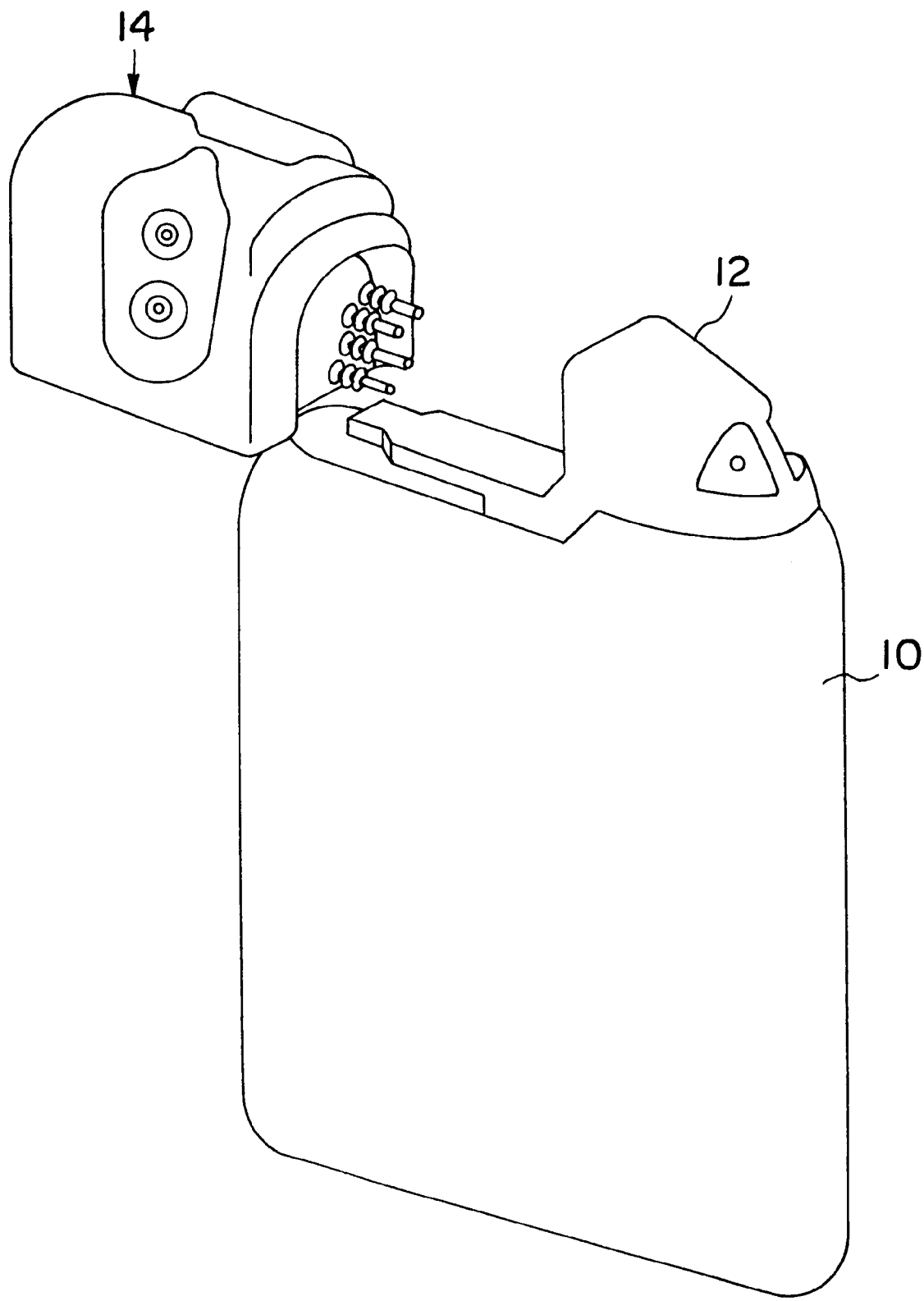
FIG. 1 is a perspective view of an implantable pacemaker/cardioverter/defibrillator employing a two module connector block according to the present invention.

FIG. 1 illustrates an implantable pacemaker/cardioverter/defibrillator 10 which has a fixed connector module 12 mounted to its upper edge surface. A mountable connector module 14 is visible, ready to be attached to the first connector module 12 which is permanently affixed to the implantable pacemaker/cardioverter/defibrillator 10.

Pacemaker/cardioverter/defibrillator 10 may correspond to any of the various commercially available implantable pacemaker/cardioverter/defibrillators, with the substitution of fixed connector module 12 for the connector block assembly otherwise present. The present invention may be practiced in conjunction with implantable pacemaker/cardioverter/defibrillators, for example as disclosed in U.S. Pat. No. 5,545,186 issued to Olson et al., U.S. Pat. No. 5,354,316 issued to Keimel, U.S. Pat. No. 5,314,430 issued to Bardy, U.S. Pat. No. 5,131,388 issued to Pless, or U.S. Pat. No. 4,821,723 issued to Baker et al., all incorporated herein by reference in their entireties. These devices may be employed directly in conjunction with the present invention, with the caveat that the feedthroughs which interconnect the circuitry therein to their connector blocks should be located such that ready access can be had from the feedthroughs to the electrical connectors within the connector bores of fixed connector module 12, as discussed below.

Alternatively, pacemaker/cardioverter/defibrillator 10 may be replaced by an implantable cardiac pacemaker, for example as disclosed in U.S. Pat. No. 5,158,078 issued to Bennett et al, U.S. Pat. No. 5,312,453 issued to Shelton et al, or U.S. Pat. No. 5,144,949 issued to Olson, or may be replaced by an implantable nerve stimulator or muscle stimulator, for example as disclosed in U.S. Pat. No. 5,199,428 issued to Obel et al. U.S. Pat. No. 5,207,218 , issued to Carpentier et al. or U.S. Pat. No. 5,330,507 issued to Schwartz, or an implantable monitoring device, such as disclosed in U.S. Pat. No. 5,331,966 issued to Bennet et al., all incorporated herein by reference in their entireties. The present invention is believed widely applicable to any form of implantable electrical device for use in conjunction with electrical leads, and is believed particularly advantageous in the contexts in which multiple electrical leads are desirable.

Figure 2:
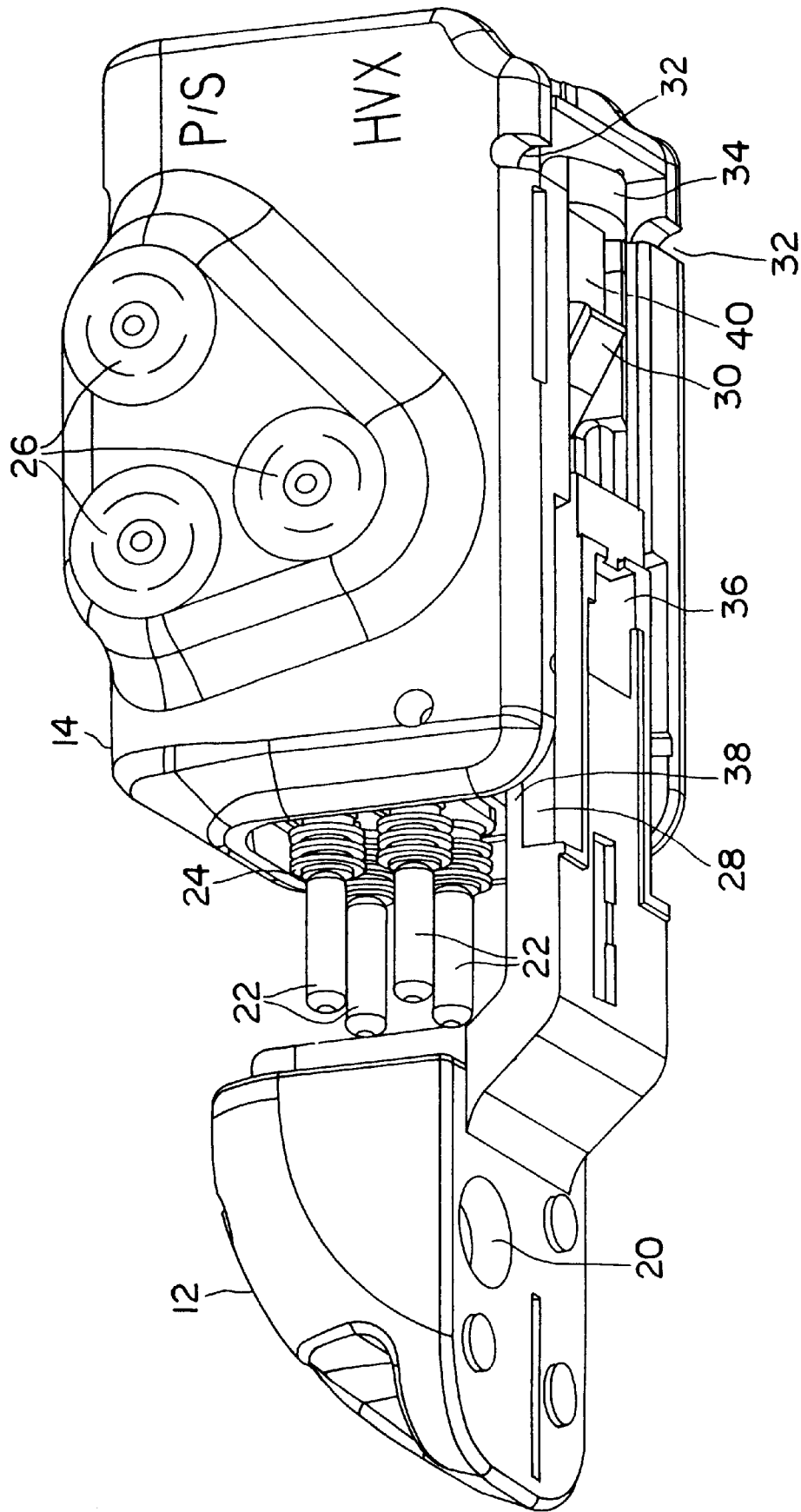
FIG. 2 is a perspective view of a two part connector block system, as illustrated in FIG. 1.

FIG. 2 is a perspective view of the fixed connector module 12 and the mountable connector module 14 of FIG. 1, shown without the associated implantable pacemaker/cardioverter/defibrillator 10. In this view, it can be seen that the mountable module 14 is provided with four connector pins 22, each provided with a set of sealing rings 24. These connector pins and sealing rings are insertable into corresponding connector bores within the fixed connector module 12, and pins 22 make electrical contact with associated electrical connectors located within the bores of fixed connector module 12. Pierceable sealing grommets 26 allow for insertion of hex wrenches to tighten set screw type connectors associated with the connector bores (not visible) of mountable connector module 14, used to accomplish electrical and mechanical coupling to pacing and defibrillation electrodes on the leads to be used with the defibrillator.

Fixed connector module 12 is provided with a mechanical mechanism for connecting to mountable connector module 14, which takes the form of a T-shaped rail 28, the outer edges 38 of which are engaged with corresponding internal grooves within the lower portion of mountable connector module 14. Connector module 14 is slid proximally along the T-rail 28 until connector pins 22 and associated sealing rings 24 are located within the connector bores of connector module 12. Connector module 14 is retained in this position by means of a latch 30 mounted on a resilient arm 40, located on the lower portion of connector module 14. As connector module 14 is moved proximally into engagement with connector module 12, resilient arm 40 is deflected upward by the action of latch 30 sliding against the distal end of the T-rail 28. At such point as connector modules 12 and 14 are fully engaged, latch 30 drops downwardly into recess 36 in T-rail 28, retaining connector module 14 on the T-rail, and retaining it on the defibrillator and in engagement with connector module 12. At the distal end of the flexible arm 14 is a camming surface 34 which provides a mechanism for removal of connector module 14. A hex wrench or other similar small tool may be inserted into either of recesses 32, sliding between camming surface 34 and the upper portion of the device enclosure, and urging resilient arm 40 upward, disengaging latch 30 from recess 36. Connector module 14 may then be removed by sliding the module distally off of T-rail 28.

Fixed connector module 12 is provided with an opening 20 in its lower surface, through which feedthrough wires from the associated implantable device may pass, so that they may be coupled to the electrical connectors associated with the bores within connector module 12. Preferably, the feedthrough from the implantable device is considered such that feedthrough wires are all located in an area allowing ready access to the connectors within connector module 12. Most preferably, the feedthroughs take the form of a multi-conductor feedthrough corresponding generally to those illustrated in U.S. Pat. No. 4,940,858, issued to Taylor et al, in U.S. Pat. No. 5,082,453 issued to Stutz, Jr. or in U.S. Pat. No. 5,144,946 issued to Weinberg et al., all incorporated herein by reference in their entireties. The feedthrough to be used in the embodiment illustrated would include four wires and preferably would be located so that it projects into opening 20, with its wires electrically coupled to the connectors within module 12.

Figure 3:
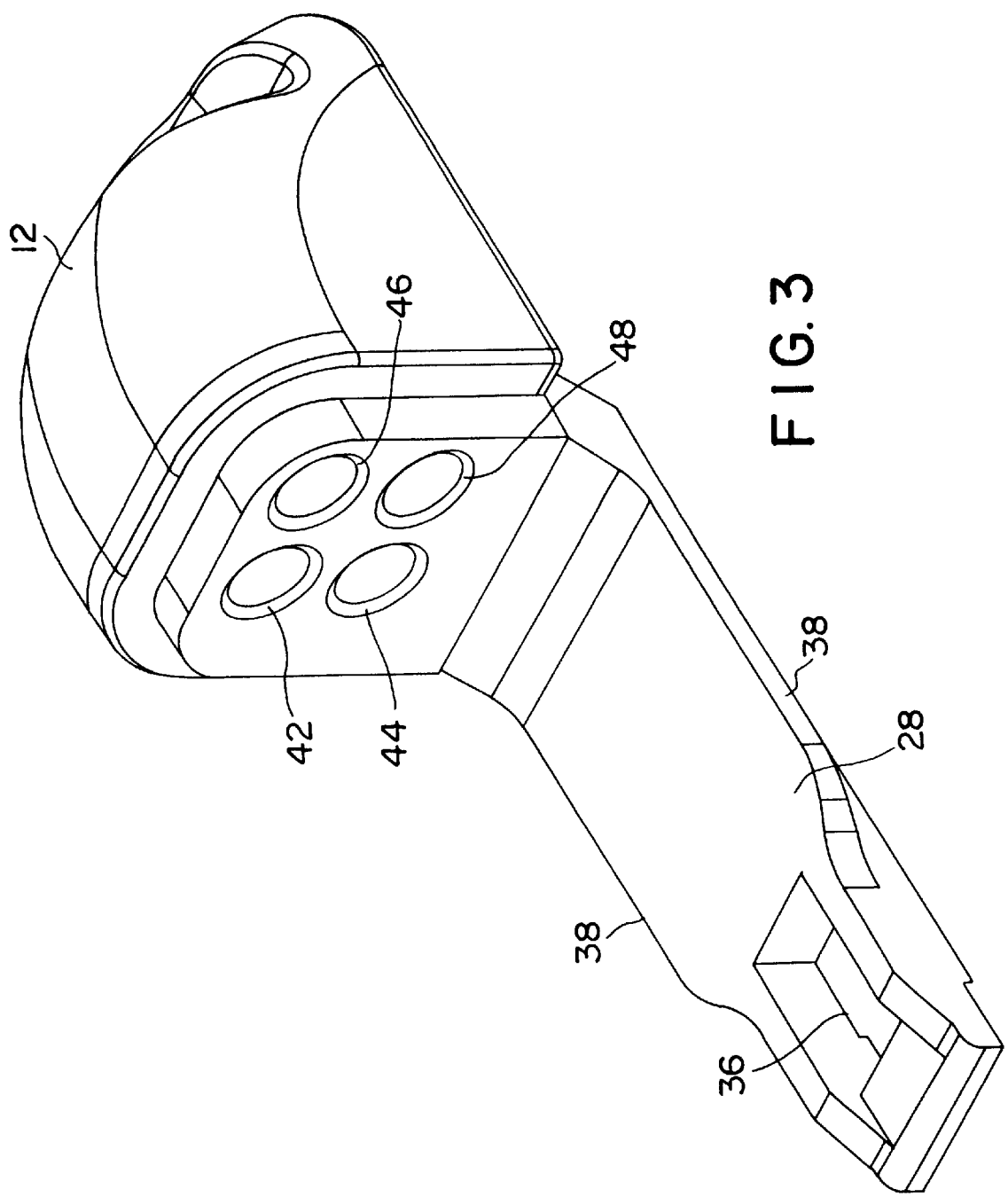
FIG. 3 is a perspective view of the fixed connector module of the two part connector block system illustrated in FIGS. 1 and 2.

FIG. 3 is a perspective view of fixed connector module 12, disassociated from the implantable pacemaker/cardioverter/defibrillator 10. In this view the configuration of T-rail 28 is clearly visible, along with associated side edges 38 which engage with mountable connector module 14. In this view, it can also be seen that connector module 12 is provided with four connector bores 42, 44, 46 and 48, each of which receives one of the connector pins 22, (FIG. 2), which is sealed within the bore by means of its associated sealing rings 24 (FIG. 2). Recess 36 is also visible in this view.

Figure 4:
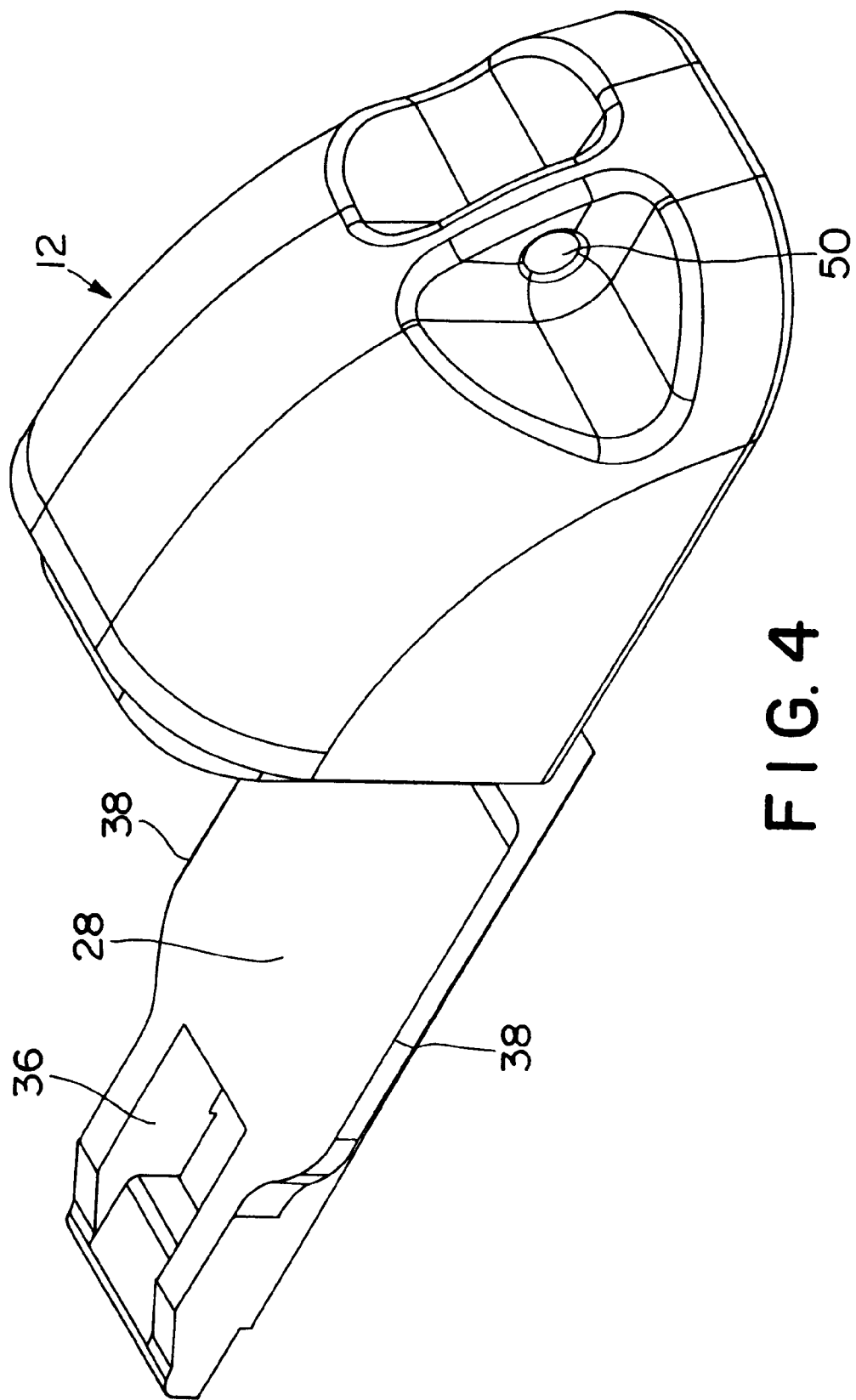
FIG. 4 is a perspective view of the fixed connector module of the two part connector block system illustrated in FIGS. 1 and 2, seen from a different angle.

FIG. 4 is a perspective view of fixed connector module 12 illustrated in FIG. 3, seen from a different angle. All labeled components correspond to those described in conjunction with FIG. 3. In this view, it can also be seen that fixed connector module 12 is provided with a suture hole 50, which may be used to stabilize the implanted pacemaker/cardioverter/defibrillator 10 in the implant pocket.

Figure 5:
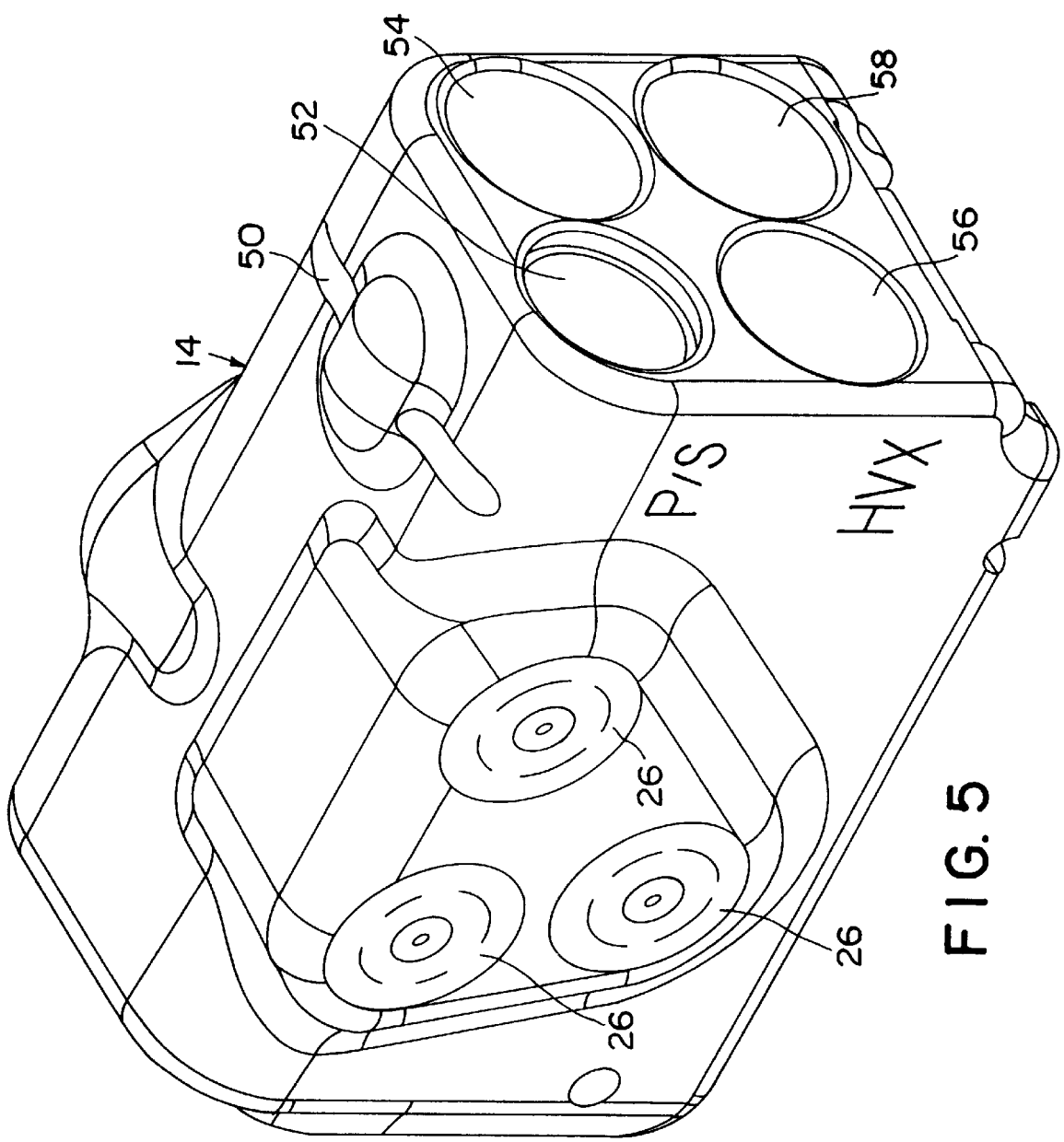
FIG. 5 is a perspective view of a first embodiment of a mountable connector module as illustrated in FIGS. 1 and 2.

FIG. 5 is a perspective view of mountable connector module 14, illustrated in FIGS. 1 and 2. In this view it can be seen that connector module 14 is provided with four connector bores, including a single IS-1 compatible 3.2 mm, bipolar, in-line connector bore 52 and three 6.5 mm connector bores 54, 56 and 58, indicating that the configuration of the connector bores and associated electrical connectors therein conforms generally to the Medtronic, Inc. "B" connector module configuration. Located within connector bore 52 are two electrical connectors adapted for coupling to the pin and ring respectively of an IS-1 type connector assembly located on an electrical lead. These connectors may be any of the connectors typically employed to couple to cardiac pacing and sensing electrodes but in this illustrated embodiment are set screw type connectors. Within each of connector bores 54, 56 and 58 is a single electrical connector adapted to couple to a connector pin on a standard 6.5 mm high voltage connector assembly mounted to an electrical lead. These connectors may be any of the connectors typically employed to couple to cardiac cardioversion and defibrillation electrodes, but in this illustrated embodiment are also set screw type connectors. Sealing grommets 26 provide access for a hex wrench to engage the set screw associated with each of the set screw type connectors within bores 52 and 56. On the opposite side of the connector assembly 14 are two additional sealing grommets, not visible, associated with the set screw type connectors in connector bores 54 and 58. A suture hole 60 is also provided, allowing an additional point of attachment of the pacemaker/cardioverter/defibrillator 10 (FIG. 1) in the implant pocket.

Figure 6:
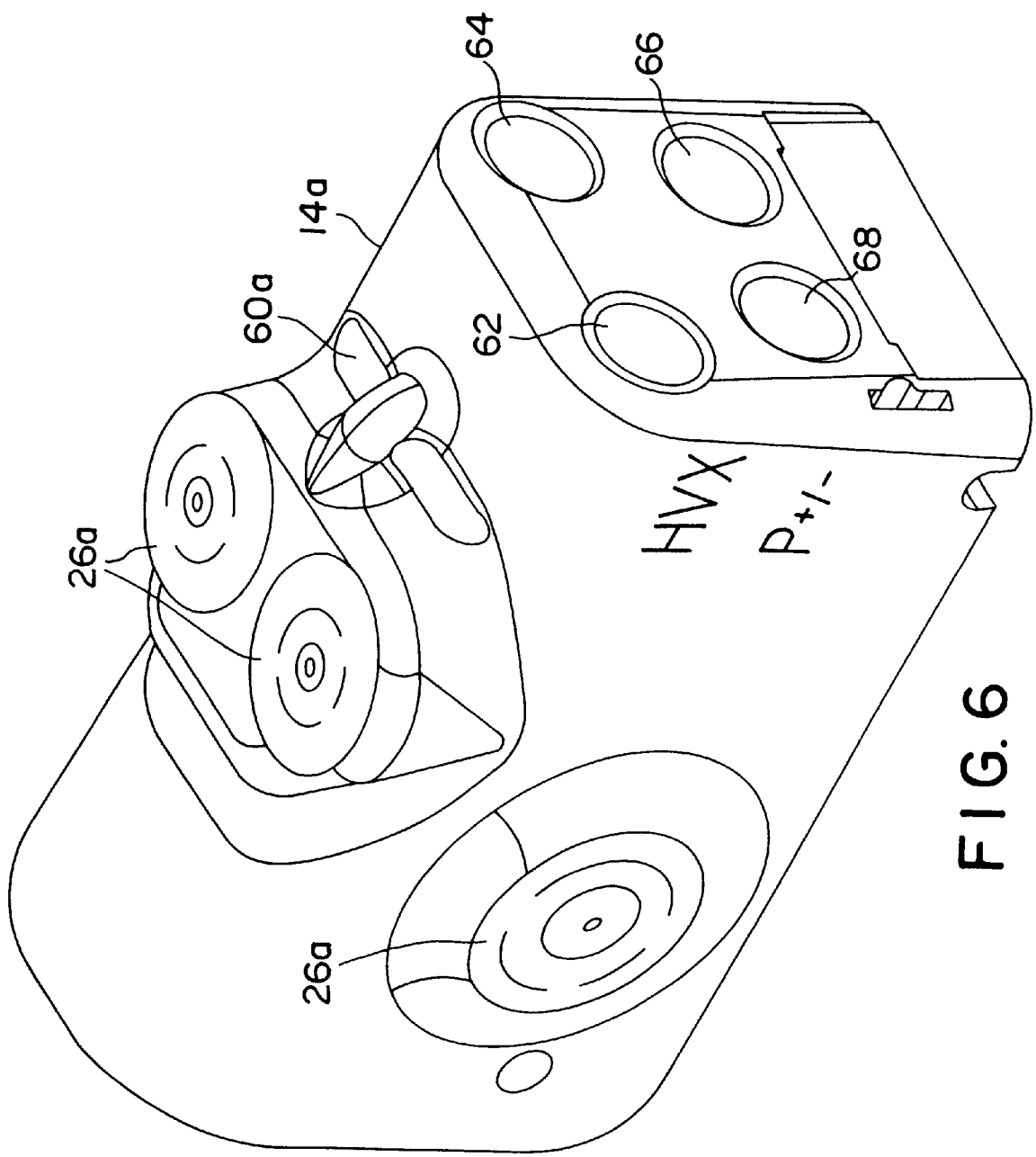
FIG. 6 is a perspective view of a second embodiment of a mountable connector module for use in conjunction with the fixed connector module illustrated in FIGS. 1–4.

FIG. 6 is a plan view of a second embodiment of a mountable connector module for use in conjunction with the fixedly module first module 12 illustrated in FIGS. 1–4. This connector module 14a, otherwise corresponding to connector module 14 discussed above, is provided with four connector bores, including a single IS-1 configuration connector bore 68 and three 3.2 mm "DF-1" configuration connector bores 62, 64 and 66. The configuration of connector module 14a thus corresponds generally to a Medtronic, Inc. "D" type connector block configuration. In this embodiment, located within IS-1 connector bore 68 are a set screw connector for engaging with a connector pin of an IS-1 configuration connector and a tool-less, spring contact electrical connector for engaging with the connector ring on the IS-1 connector inserted in the bore, both of conventional types. Each of connector bores 62, 64 and 66 is provided with a set screw type connector for coupling to a connector pin on a DF-1 high voltage electrical connector employed to couple to implantable cardioversion and defibrillation electrodes. Pierceable sealing grommets 26a allow passable of a hex wrench to engage the set screws associated with electrical connectors in connector bores 62, 64 and 68. A corresponding additional pierceable sealing grommet is located on the opposite side of the connector, allowing engagement of a hex wrench with the set screw connector associated with connector bore 66.

Figure 7:
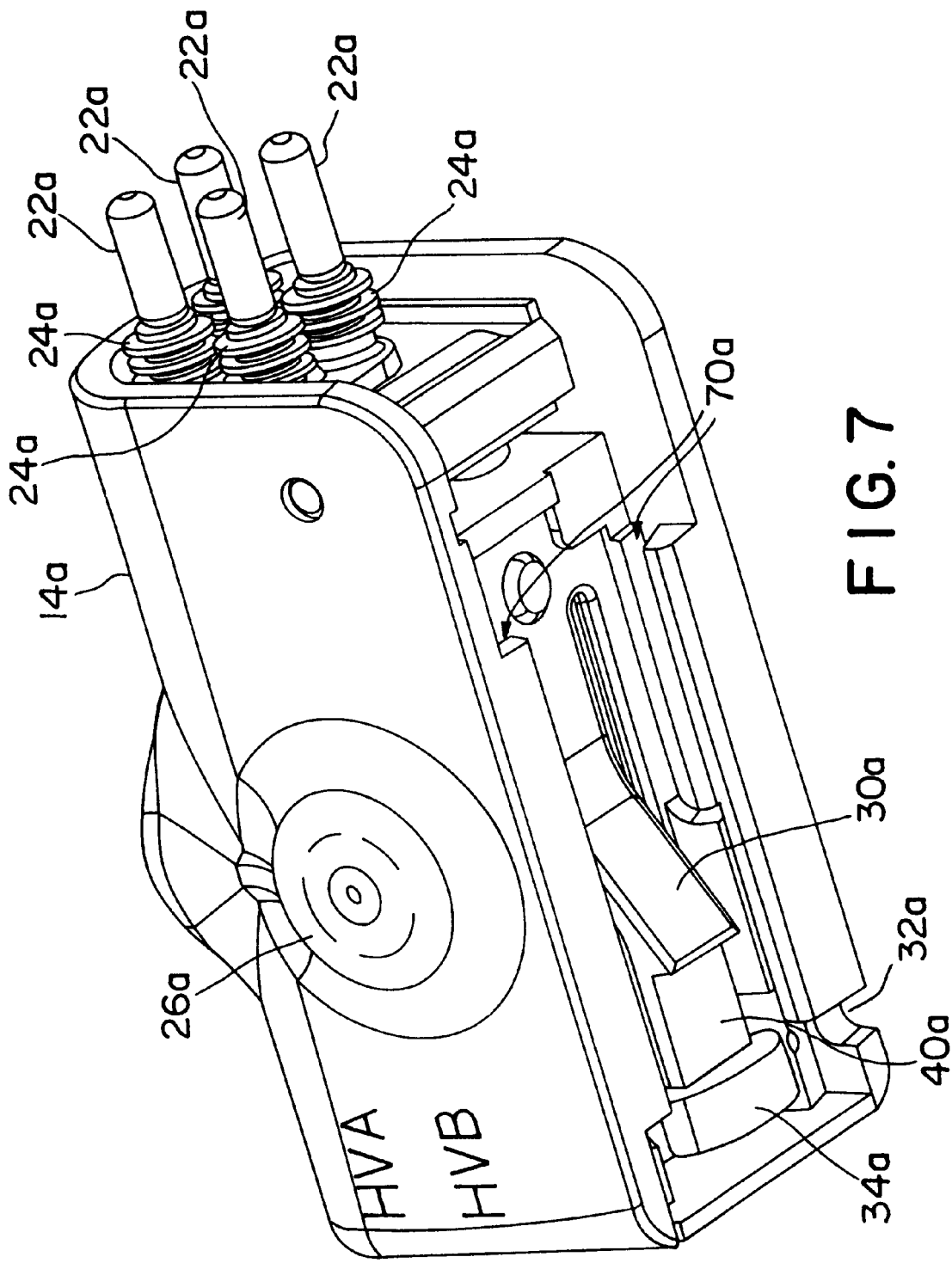
FIG. 7 is a perspective view of the mountable connector module illustrated in FIG. 6, seen from a different angle.

FIG. 7 illustrates the connector assembly 14a illustrated in FIG. 6, viewed from a different angle. Connector pins 22a and sealing rings 24a correspond exactly to connector pins 22 and sealing rings 24 illustrated in FIG. 2. It should also be understood that the mechanical configuration of the lower surface of connector assembly 14a corresponds to that of connector assembly 14, and engages with the T-rail 28 illustrated in FIGS. 3 and 4 in precisely the same manner. In this view, the structure of deflectable resilient arm 40a is more readily apparent, along with the ramped configuration of latch 30a. Labeled elements 30a, 32a, 34a and 40a all correspond precisely to elements 30, 32, 34 and 40, illustrated in FIG. 2 in conjunction with connector module 14. In this view, internal slots 70a which engage the edges 38 of T-rail 28 (FIG. 3) are also visible. The configuration of slots 70a likewise corresponds to the configuration of the internal slots provided in connector module 14, but not visible in FIG. 3.

Figure 8:
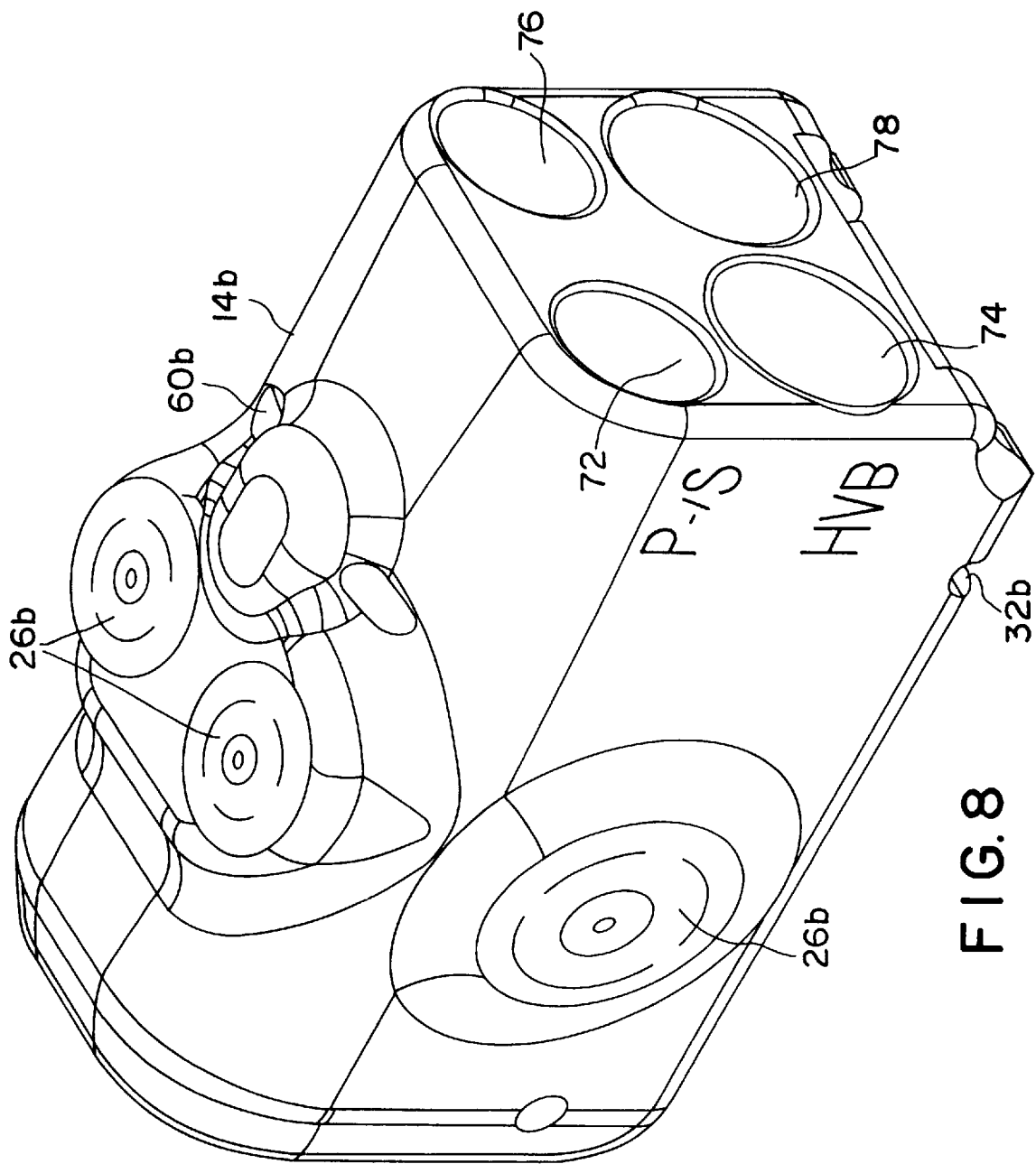
FIG. 8 is a perspective view of a third embodiment of a mountable connector module for use in conjunction with fixed connector module illustrated in FIGS. 1–4.

FIG. 8 is a perspective drawing of a third embodiment of a mountable connector module 14b, appropriate for use in conjunction with the fixedly mounted connector module 12 illustrated in FIGS. 3 and 4. This connector module corresponds to connector module 14, illustrated in FIGS. 3 and 6, with the exception that it is provided with four connector bores 72, 74, 76 and 78, including two 5 mm unipolar connector bores 72 and 74 and two 6.5 mm connector bores 76 and 78. The configuration of connector module 14b thus corresponds generally to a Medtronic, Inc. "E" type connector block configuration. Connector bores 72 and 76 are provided with a set screw type internal electrical connector, and are adapted to receive unipolar or bifurcated connector assemblies associated with cardiac pacing and sensing leads. Connector bores 74 and 78 are each provided with a single set screw type connector and are adapted to receive 6.5 mm high voltage electrical connectors mounted to implantable electrical leads of the type which typically carry cardioversion and defibrillation electrodes. Pierceable sealing grommets 26b provide access to the set screw type connectors in bores 72, 74 and 78. A similar pierceable sealing grommet is located on the opposite side of the connector module 14b, for access to the set screw type connector located in connector bore 78. A suture hole 60b is provided to assist in affixing the implantable pacemaker/cardioverter/defibrillator 10 to the tissue within the implant pocket. Connector module 14b interfaces and interconnects with connector module 12 (FIGS. 3 and 4) in precisely the same fashion as connector modules 14 and 14a, described above.

The family of the three removably mountable second connector modules, 14, 14a and 14b are all preferably provided to the physician in conjunction with the associated implantable pacemaker/cardioverter/defibrillator. Thus, on implant, the physician will likely be able to couple whatever set of leads he has chosen to employ to the implantable defibrillator, without the necessity of locating and employing a lead adapter or lead connector. The physician simply determines which of the three connector modules is appropriate, slides it onto the implantable defibrillator by sliding it proximally along the T-rail until a snap or click is heard indicating that the ramped latch 30 (FIG. 2) has engaged in recess 36 (FIG. 2). At this point, the electrical connectors within the connector bores of the selected connector module 14, 14a, 14b are connected to the circuitry within the implantable pacemaker/cardioverter/defibrillator in precisely the same fashion that would have been true had the connector block been provided as a single, molded assembly. The overall configuration of the resultant assembled device closely resembles that of a device provided with a connector assembly, and thus requires no substantial enlargement of the pocket as would be required in conjunction with typical lead converter or adapter systems.

In the event that it is necessary to change the leads associated with the device, the mountable connector module, e.g. module 14 (FIG. 2), mounted to the device, may be removed by simply inserting the same hex wrench employed to tighten the set screw type connectors on the module into recess 32 to lift the latch 30 out of recess 36 allowing the connector module to simply be slid off the T-rail 28 and replaced with an appropriate substitute connector module. As the design of implantable leads progresses, it may also be possible to include replacement or updated mountable connector modules in conjunction with the updated leads, so that they may be readily attached to previously implanted devices if necessary, or may be attached to devices which were not supplied with updated connector modules at the time of manufacture. Overall, the system of two-part connector modules set forth provides a high degree of flexibility and adaptability, allowing the physician to implant leads and pulse generators as he or she deems best, without significant additional complexity or size as would be required in conjunction with present day adapters and converters.

Figure 9:
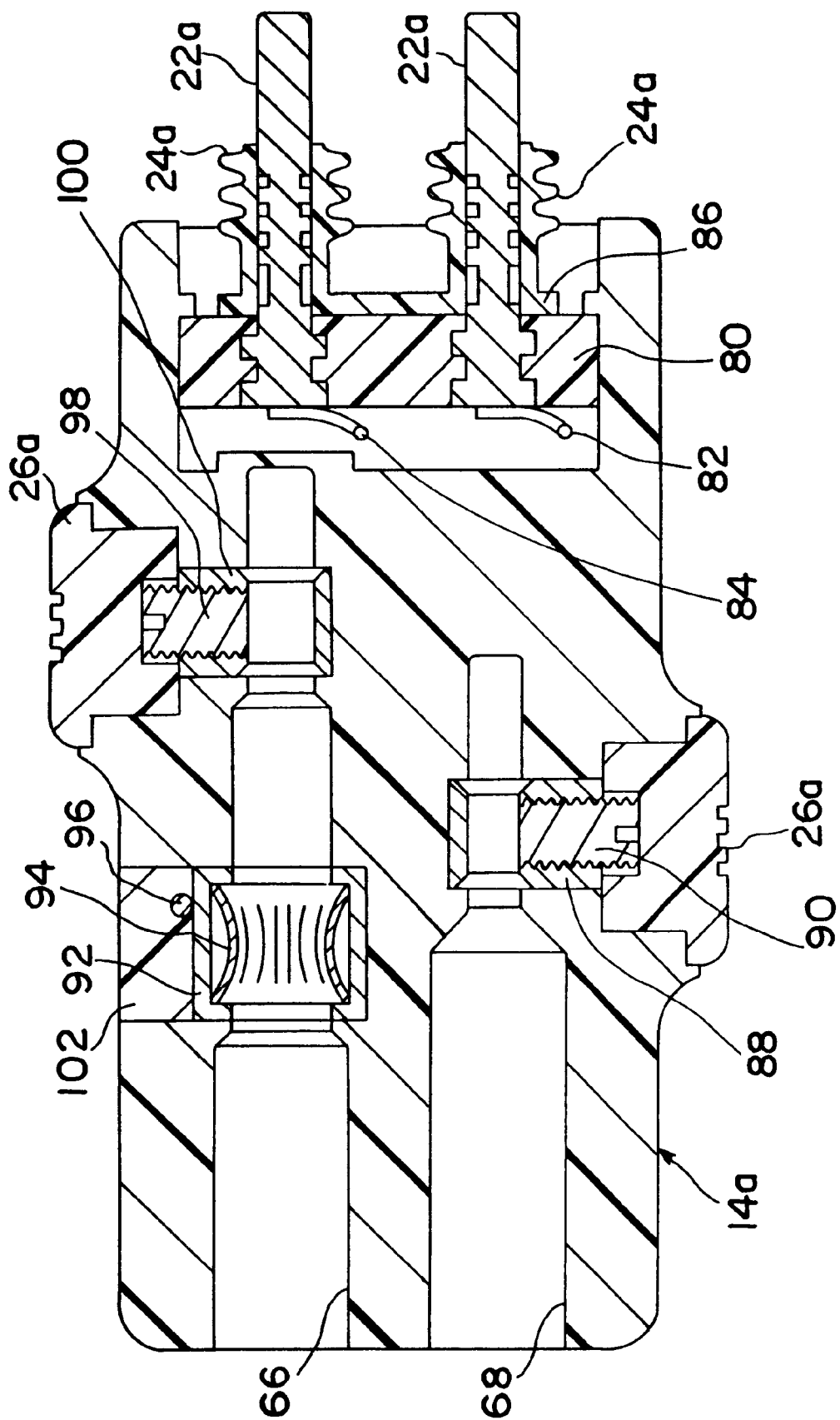
FIG. 9 is a cross-sectional view through the mountable connector module illustrated in FIGS. 6 and 7.

FIG. 9 is a cross section view through module 14a, illustrated in FIGS. 6 and 7, illustrating the internal structure of the connector bores, electrical connectors and connector pins of the device. This structure is exemplary of the internal structures of all of the illustrated connector modules 14, 14a and 14b, with set screw and toolless spring contact connectors employed as discussed above.

IS-1 bore 66 is provided with two electrical connectors including a "tool-less" connector comprising a conductive ferrule 92 and an internal spring contact 94, of a type conventionally used in conjunction with implantable cardiac pacemakers and cardioverter/defibrillators, as disclosed in U.S. Pat. No. 5,207,218, issued to Carpentier et al., cited above. Spring 94 engages the connector ring on an IS-1 type lead connector. Visible in cross-section is a wire 96 which is welded to ferrule 92, to allow interconnection between ferrule 92 and one of the connector pins 22a. Each of the electrical connectors within connector module 12 are coupled to one of the connector pins 22a by means of such wires, which are passed through grooves molded into the connector block, which grooves are later back filled with silicone rubber, as is conventional in the manufacture of connector blocks for cardiac pacemakers and cardioverter/defibrillators. The aperture through which ferrule 92 is inserted is backfilled by medical adhesive 102. The second electrical connector associated with connector bore 66 is a set screw type connector, comprising a conductive connector 100 and an internal set screw 98, of a type conventional for use in conjunction with implantable pacemakers and cardioverter/defibrillators. Pierceable sealing grommet 26a is also visible in cross-section, allowing access to set screw 96 by means of a hex wrench. 3.2 mm "DF-1" connector bore 68 is also visible in cross-section, provided with a set screw connector comprising a connector 88 and an associated set screw 90, arranged to be accessed to the pierceable sealing grommets 26a.

At the proximal end of connector module 114a, pins 22a and associated sealing rings 24a are visible. In this view it can be seen that sealing rings 24a are molded integral to a base plate 86. Connector pins 22a are mounted within a molded plastic member 80, in turn mounted within connector block 14a. Wires 82 and 84 are visible spot welded, soldered or wire bonded to the proximal ends of connector pins 22a and, although not visible in this Figure, extend to one or more of the electrical connectors within module 14a.

The above illustration is exemplary for all of the removably mounted connector modules 14, 14a and 14b, with set screw type connector substituted in some cases for the tool-less connector, for use in conjunction with the IS-1 connector bore. In conjunction with the connector assemblies 14, 14a and 14b illustrated, it should be noted that each of the connector modules is provided with four connector pins, while the "B" and "D" connector module configurations of modules 14 and 14a each include five electrical connectors. In these configurations, two of the connectors for cardioversion/defibrillation electrodes are connected in common to one of the connector pins 22, 22a.

Figure 10:
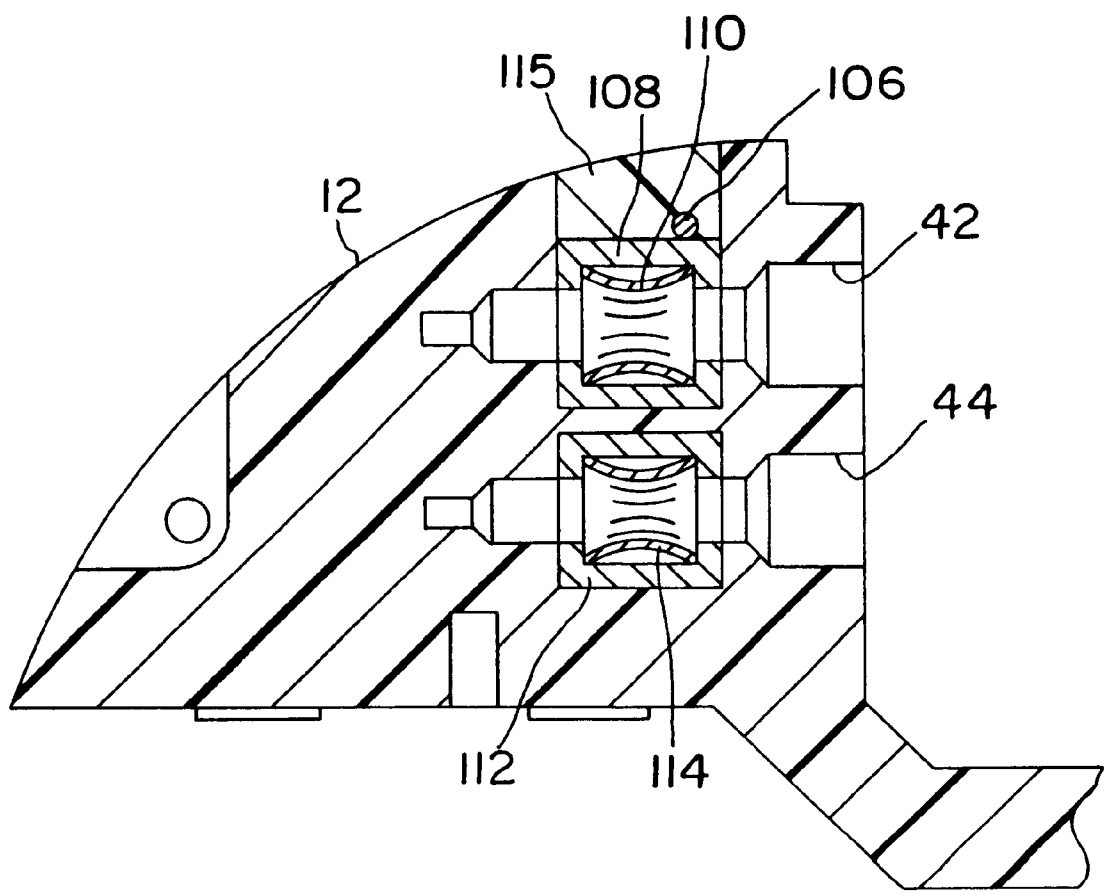
FIG. 10 is a cross-sectional view through a portion of the fixed connector module illustrated in FIGS. 3 and 4.

FIG. 10 is a sectional view through the first connector module 12, illustrated in FIGS. 1–4, taken along a plane passing through connector bores 42 and 44. Connector bore 42 is provided with a tool-less electrical connector comprising a ferrule 108 and an internal spring member 110 of the sort conventionally used in conjunction with implantable pacemakers and cardioverter/defibrillators, as described above. A wire 106, laser welded to ferrule 108 allows for interconnection of the ferrule to the feedthrough wires extending from the associated implantable pacemaker/cardioverter/defibrillator 10 (not illustrated). The aperture through which ferrule 108 was inserted is backfilled with medical adhesive 15. Routing of wires from the feedthrough pins of the associated implantable defibrillator to the ferrules is accomplished by means of pre-molded grooves and slots which are later backfilled with medical adhesive, as is conventional in the manufacture of connector blocks for implantable pacemakers and cardioverter/defibrillators. Connector bore 44 also has an associated tool-less connector comprising a ferrule 112 and spring member 114. Each of the other two connector bores 46 and 48, not illustrated, are provided with identical tool-less connectors, each coupled to one feedthrough wire extending from the associated pacemaker/cardioverter/defibrillator (not illustrated).

Figure 11:
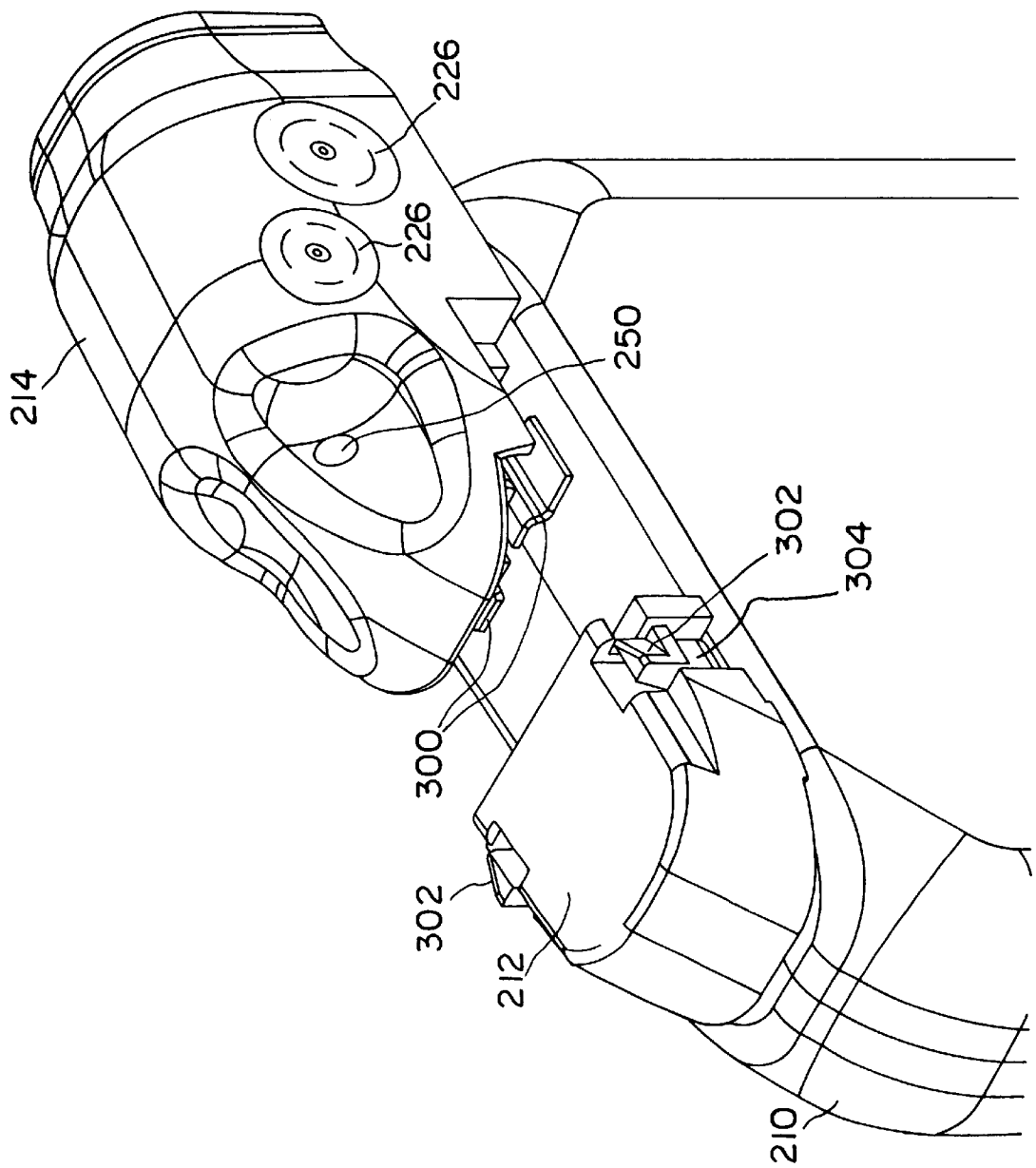
FIG. 11 is a perspective view of an implantable defibrillator in conjunction with a second embodiment of a two-part connector block system.

FIG. 11 is a perspective drawing of a second embodiment of a two-part connector block system. Like the first embodiment of a two-part connector block system described above, the system includes a fixed connector module 212, fixedly mounted to the upper edge surface of an implantable pacemaker/cardioverter/defibrillator or other electrical medical device 210 and a mountable connector module 214. Mountable connector module 214 corresponds generally in structure to the mountable connector modules 14, 14a and 14b described above, with the exception that it employs a different interconnection mechanism for mounting the module to the housing of the device 210, and as visible in FIG. 12, employs fewer interconnections to the circuitry within the device 210.

Module 214 is retained on the housing of the implantable device 210 by means of metal clips 300, welded to the housing, which engage with a corresponding metal clip (not visible) on the lower surface on module 214. Module 214 is slid proximally to engage its connector pins (not visible in this view) with the connector bores (not visible in this view) of fixed module 212. Inadvertent removal of module 214 is prevented by means of latches 302 which are formed as part of a U-shaped resilient plastic member 304. Once connector module 214 is slid proximally into engagement with connector module 212 latches 302 engage with the recesses on the lower surface of connector module 214 to prevent inadvertent removal. Removal of connector module 214 is accomplished by compression of U-shaped member 304 to move latches 302 inward, allowing module 214 to be slid distally and removed.

Figure 12:
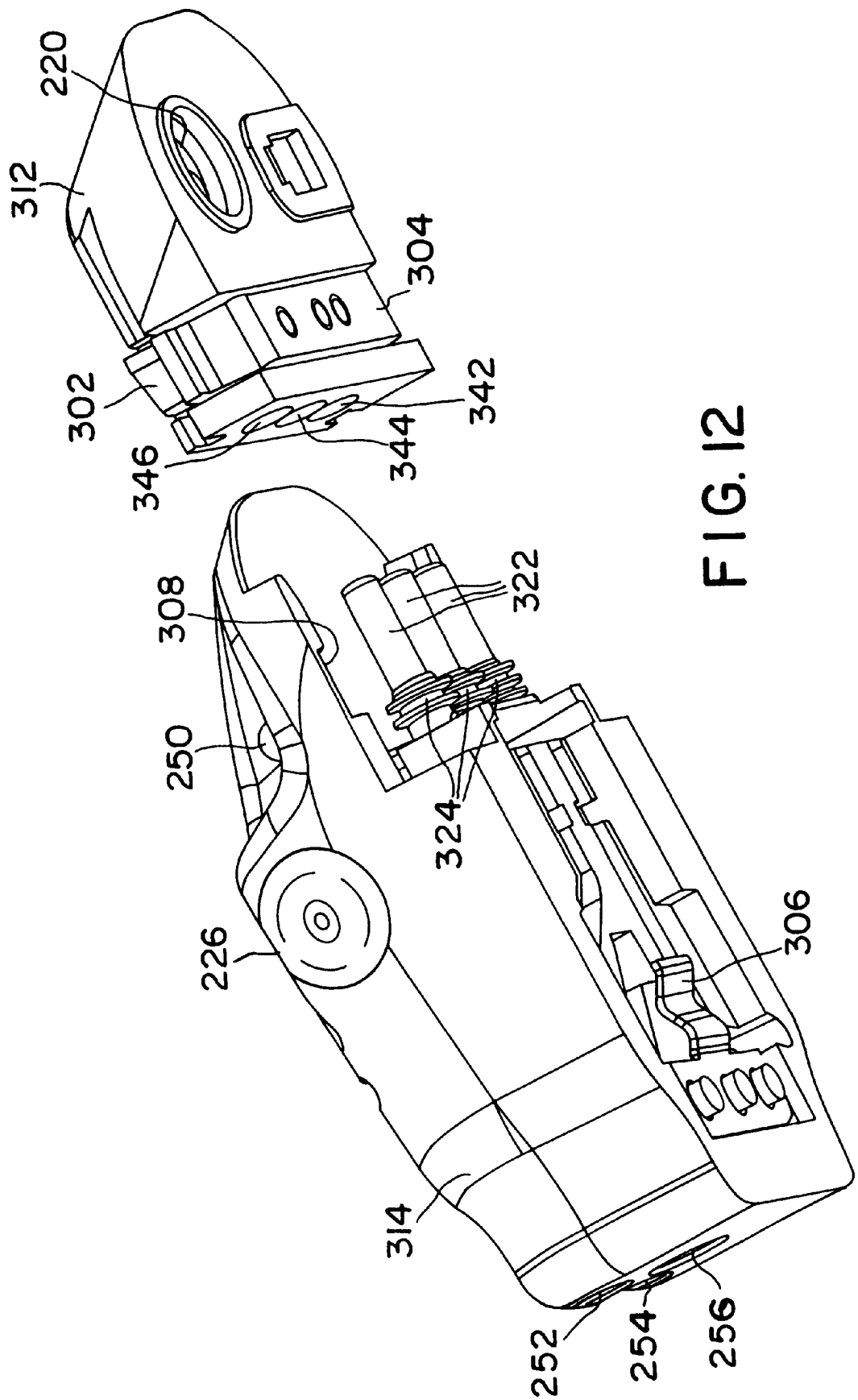
FIG. 12 is a perspective view of the two part connector block system illustrated in FIG. 11, removed from the implantable defibrillator.

FIG. 12 is a perspective view of the two-part connector system illustrated in FIG. 11, absent the associated implantable medical device 210. In this view, it can be seen that fixed connector module 312 is provided with three connector bores, 342, 344 and 346, which correspond to the connector bores 42, 44, 46 and 48 of connector module 12 illustrated in FIGS. 1–4 and contain tool-less spring contact connectors as illustrated in FIG. 10 and described above. The configuration of U-shaped, resilient member 304 is also visible in this view, along with aperture 220, which allows passage of the feedthrough wires from the associated medical device into contact with connectors in connector bores 342, 344 and 346 as discussed above.

Mountable connector module 314 is also provided with three connector bores, 252, 254 and 256, each containing one set screw type connector coupled by means of an internal wire to one of connector pins 322. Each of connector pins 322 is provided with sealing rings 324 to allow sealing of the connector pins within the bores 342, 344 and 346 of module 312. Pierceable sealing grommets 226 allow passage of a hex wrench to the set screw connectors within connector bores 252, 254 and 256. A suture hole 250 is provided to assist in securing the device to the tissue in the implant pocket.

In this view, metal clip 306 is visible, which engages metal clips 300, illustrated in FIG. 11. As connectors 322 are slid into connector bores 342, 344 and 346, clip 306 slides underneath and frictionally engages clips 300. If it is desired to employ the housing of the device 210 as an electrode, and also to provide for the possibility of connecting one or more electrodes on the associated lead system with the housing, clip 306 may also be employed as an electrical connector for interconnecting a connector within one of the connector bores with the device housing, if desired. Also visible in this view is one of the internal notches 308 which engages latch 302, preventing inadvertent removal of the connector block 314.

Figure 13:
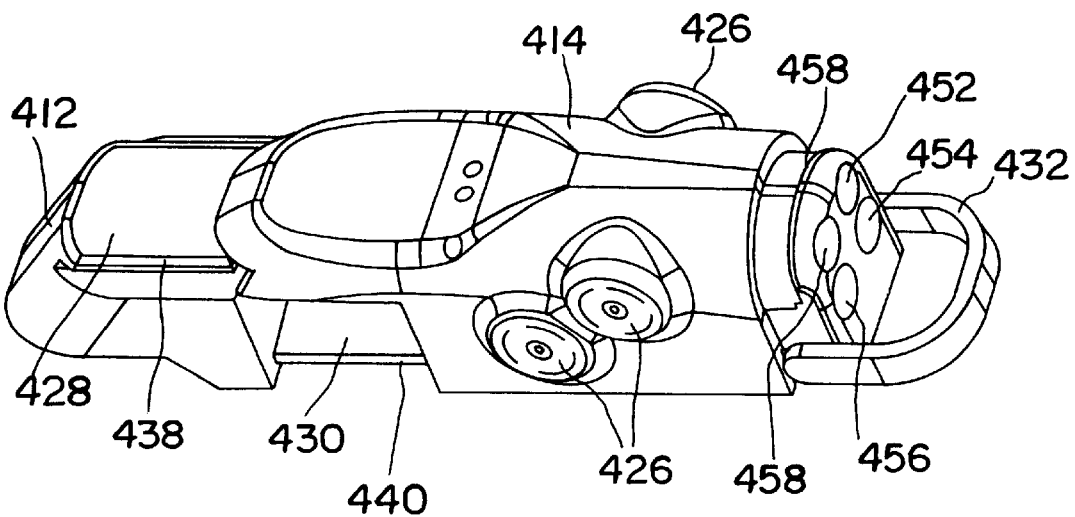
FIG. 13 is a perspective view of a third embodiment of a two part connector block system.
Figure 14:
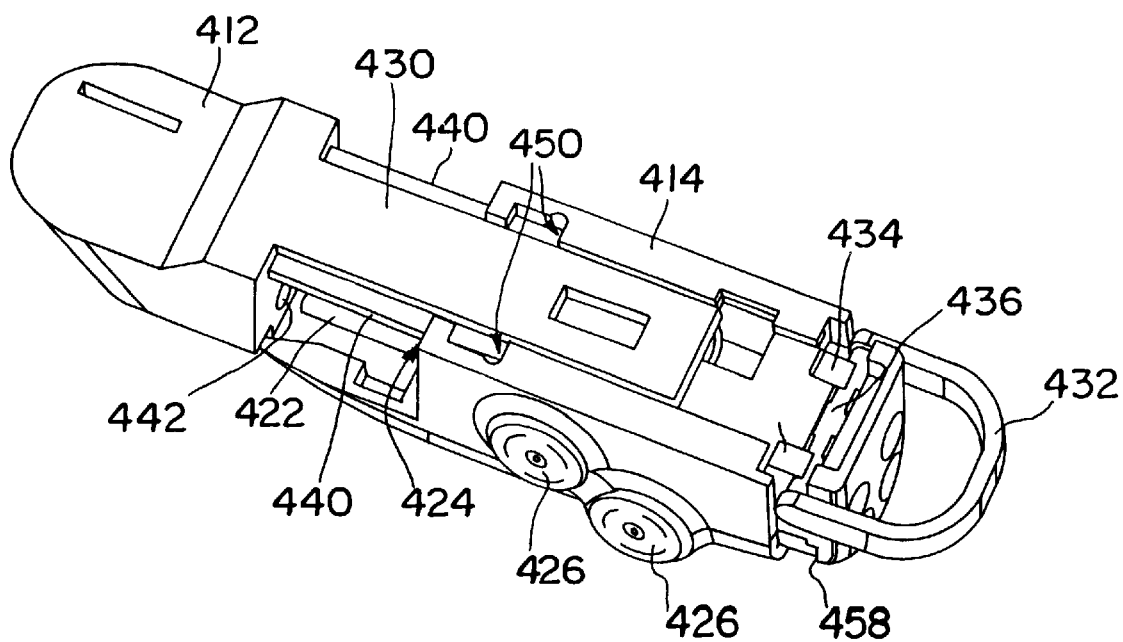
FIG. 14 is a perspective view of the two part connector block system illustrated in FIG. 13, viewed from a different angle.

FIG. 13 is a perspective view of a third embodiment of a two-part connector system according to the present invention. The two-part connector system includes a fixed module 412 which is to be mounted to an edge surface of a housing of an implantable medical device and a mountable module 414. Mountable module 414 is provided with four connector bores, 452, 454, 456 and 458, each including a set screw type electrical connector accessible by means of pierceable sealing grommets 426. In this embodiment of the invention, two T-rails are provided including a first T-rail 428 having outer edges 438, mounted to the upper portion of the fixed module 412, and a second T-rail 430, having outer edges 440, extending along the edge of the connector housing, similar to that illustrated in FIGS. 3 and 4 above. Mountable module 414 is provided with corresponding internal grooves, which engage the edges 438 and 440 of T-rails 428 and 430, in the same fashion as described above in conjunction with T-rail 28 illustrated in FIGS. 3 and 4. A pivoting handle 430 is employed both as a mechanism for assisting in removal of mountable module 414 and as part of a latching mechanism for preventing inadvertent removal, as illustrated in FIG. 14 below. A "U" shaped groove 458 is sized to receive handle 430 when it is pivoted upward.

FIG. 14 shows a plan view of the two-part connector system illustrated in FIG. 13, taken from a different angle. In this view, one of connector pins 422 and associated sealing rings 424 is visible, along with one of connector bores 442 in fixed module 412. Connector pins 422 and the connector bores 442 function in precisely the same fashion as described above in conjunction with the first and second embodiments of the two-part connector block system, described above. T-rail 430 is visible, with its edges 440 shown engaging internal grooves 450 in the lower surface of mountable connector module 414.

Connector module 414 is provided with a retention and latching mechanism which includes the handle 432 which is mounted to a rotatable rod 436 which carries two lugs 434. When mountable connector module 414 is fully engaged with fixed connector module 412 with connector pins 422 inserted into connector bores 442, handle 432 is pivoted upward, pivoting lugs 434 downward and into engagement with corresponding recesses formed in the upper surfaces of T-rail 430, to prevent inadvertent removal of connector module 414. Handle 432 latches into U-shaped groove 458 to prevent inadvertent movement of handle 432 after implant.

FIGS. 15a, 15b, 16a, 16b, 17a and 17b are perspective drawings illustrating a fourth embodiment of a two-part connector block system according to the present invention. In this embodiment, the implantable device 510 is provided with a fixed connector block module 512, mounted so that the connector bores within (not visible in this view) face upward toward the upper edge surface 532 of the device, rather than facing parallel thereto, as in the first, second and third embodiments of the invention described above. In this embodiment, the mountable connector module 514 is provided with downwardly extending pins 522, each is provided with an associated set of sealing rings 524 for insertion into the corresponding connector bores within fixed connector module 512. When fully inserted, a metal spring latch 530 engages with a corresponding recess on the lower surface of mountable connector module 514 to retain the module in place on the upper edge surface 532 of the device. FIG. 15b illustrates the mountable connector module 514 inserted into fixed connector module 522 and fully installed on the upper edge surface 532 of device 510. FIG. 16a illustrates device 510 in conjunction with an alternative mountable connector module 514a, provided with connector pins 522a and associated sealing rings 524a, insertable into the corresponding connector bores of fixed connector module 512. Mountable connector module 514 is retained on upper edge surface 532 by means of spring clip 530. FIG. 16b shows mountable module 514 inserted into fixed module 522 and thereby mounted to the upper edge surface 532 of device 510.

FIG. 17a illustrates an alternative mechanism which may be used in conjunction with the device 510, if all electrodes desired to be used with the device are located on a single lead 516. In this case, rather than employing a connector block having its own connector bores, the lead 516 is provided with a molded connector assembly 514b having connector pins 522b and sealing rings 524b corresponding to the connector pins and sealing rings of mountable connector modules 514 and 514a. In this case, the connector assembly 514 is retained on the upper edge surface 532 of device 510 by means of spring clip 530, which engages with a recess 534. If connector assembly 514 is fabricated of a slightly resilient material, lead assembly 514 may be removed from the device 510 by twisting it slightly to disengage recess 534 from clip 530. FIG. 17b illustrates lead 516 with connector assembly 514b fully inserted into fixed connector module 512, retained along the upper edge surface 532 of the device 510.

The connector block system illustrated in FIGS. 15, 16 and 17, provides an additional benefit over the two-part connector block systems in the first three embodiments, in that it provides for the ability to substantially reduce the overall size of the device in those circumstances in which only a single lead is to be employed. It should also be understood in the context of the first three embodiments of the two-part connector systems described above, that a connector assembly molded to or permanently attached to one or more leads might be substituted for the mountable connector block 14, 14a, 14b, inserted into the connector bores of the fixed connector module 512, and retained on the device housing in precisely the same manner.

Figure 18:
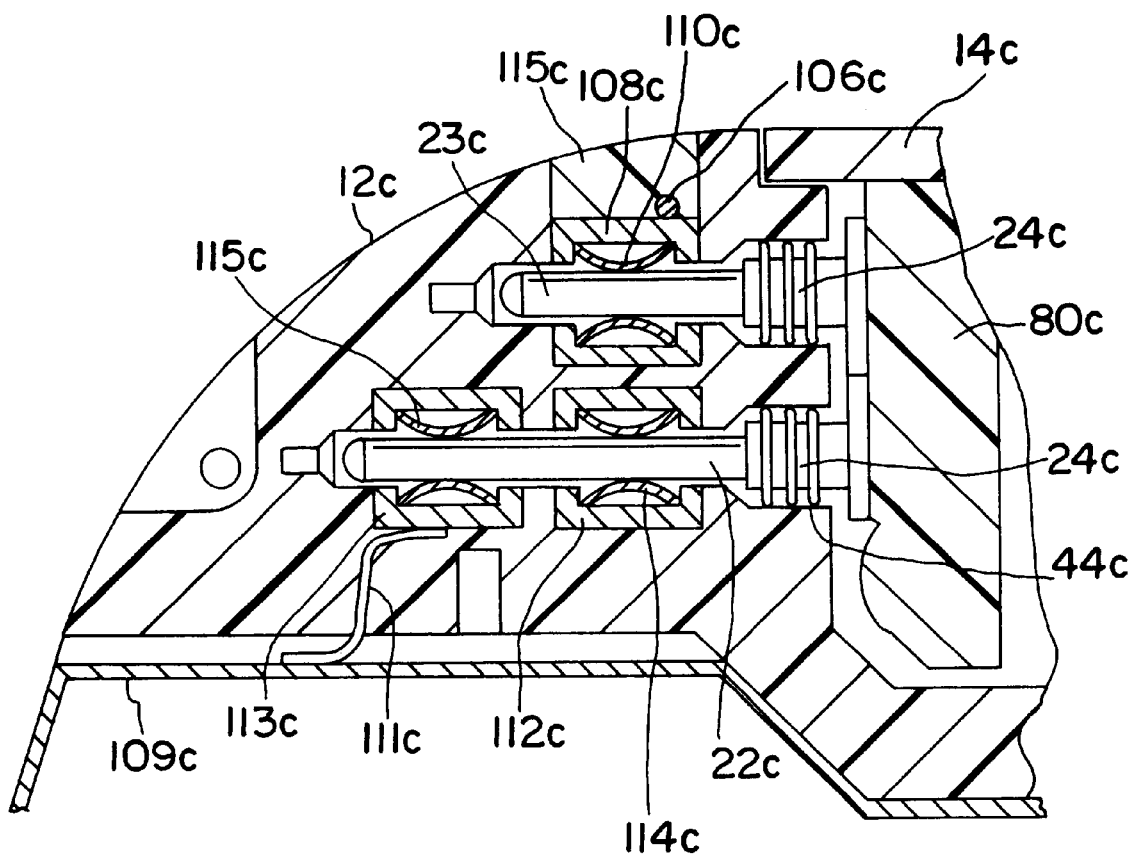
FIG. 18 is a sectional view through a fifth embodiment of a two part connector block system according to the present invention.

FIG. 18 is a sectional view through an alternative embodiment of a first connector module 12c, taken along a plane passing through connector bores 42c and 44c in conjunction with an additional alternative embodiment of a second connector module 14c. Connector bore 42c is provided with a tool-less electrical connector comprising a ferrule 108c and an internal spring member 110c of the sort conventionally used in conjunction with implantable pacemakers and cardioverter/defibrillators, as described above. A wire 106c, laser welded to ferrule 108c allows for interconnection of the ferrule to the feedthrough wires extending from an associated implantable pacemaker/cardioverter/defibrillator (not illustrated). The aperture through which ferrule 108c was inserted is backfilled with medical adhesive 15c. Routing of wires from the feedthrough pins of the associated implantable defibrillator to the ferrules is accomplished by means of pre-molded grooves and slots which are later backfilled with medical adhesive, as is conventional in the manufacture of connector blocks for implantable pacemakers and cardioverter/defibrillators. Connector bore 44c also has an associated tool-less connector comprising a ferrule 112c and spring member 114c. Each of the other two connector bores, not illustrated, are provided with identical tool-less connectors, each coupled to one feedthrough wire extending from the associated pacemaker/cardioverter/defibrillator (not illustrated). This much of the structure corresponds to that illustrated in FIG. 10.

In addition to the structure illustrated in FIG. 10, module 12c is provided with an additional electrical connector comprising a conductive ferrule 113c an a spring contact 115c. Ferrule 113c is coupled to the device housing 109c by means of conductor 111c. As illustrated, module 14c is provided with connector pins 22c and 23c each provided with sealing rings 24c corresponding to the connector pins 22a an sealing rings 24a illustrated in FIG. 7, with the exception that pin 22c as illustrated is of increased length, enabling it to contact both connectors associated with connector bore 44c. In a manner analogous to that illustrated in U.S. Pat. No. 5,374,279 issued to Duffin et al. and incorporated herein by reference in its entirety, connector pin 22c may be employed to connect the housing 109c of the defibrillator to the defibrillation pulse generator therein. Depending on the particular implementation chosen for module 14c, connector pin may also be connected to an electrical connector associated with a connector bore within module 14c, allowing connection to an defibrillation electrode on an associated lead. A second module employing a shorter pin instead of pin 22c, for example connector module 14a, illustrated in FIG. 7 may be also be inserted in first module 12c, with the result that the housing 109c would not serve as an electrode. Other optional interconnections may correspondingly be provided by employing additional or different arrangements of connector bores having multiple connectors in module 12c and different interconnections between connectors in module 12c in conjunction with different numbers or arrangements of elongated connector pins in module 14c.

In the above embodiments, a number of different mechanical mechanisms are disclosed for retaining the removable connector module adjacent the fixed connector module, along the edge of an implantable medical device. These mechanical interconnection mechanisms include several embodiments which are believed to be particularly advantageous for use in conjunction with a two-part connector system. However, other mechanical interconnection mechanisms could be substituted for those illustrated while retaining the benefit of the two-part connector system. Substitute mechanical interconnection systems should preferably provide for a mechanical interlock of the multiple connector with the fixed connector and/or the device housing concurrent with insertion of the connectors on the mountable module into the connector bores of the fixed module. It should also be noted that a reversal of elements, such that the fixed connector module is provided with a set of connector pins insertable in corresponding bores on the mountable connector module is also believed workable in the context of the present invention, as would the substitution of other electrical interconnection systems for connector pins and connector bores as disclosed herein. Finally, while the connector block systems as disclosed above are all arranged along an edge surface of the device housing, as is conventional, it may alternatively be arranged on a side surface of a device housing. As such, the above disclosure should be considered exemplary, rather than limiting, with regard to the claims which follow. In conjunction with the above specification, we claim:

We claim:

1. A system for connecting to electrical leads having connector assemblies carrying electrical connectors, comprising:

an implantable electrical device havino a device housing containing electrical circuitry and having a first connector module fixedly mounted to the device housing and having a first set of electrical connectors coupled to the circuitry within the device housing;

a second connector module having a second set of electrical connectors engageable with the first set of connectors and a third set of connectors electrically coupled to the second set of connectors and engageable with the connectors on the electrical leads; and means for retaining the second module on an outer surface of the device housing adjacent the first module while the second set of connectors engages the first set of connectors;

wherein the first and second sets of connectors comprise means for engaging with one another as a result of movement of the second module in a first direction with respect to the first module and wherein the retaining means comprises means for retaining the second connector module on the outer surface of the device housing during movement of the second module in the first direction.

2. A system according to claim 1 wherein one of the first and second sets of connectors comprise connector pins extending along an axis and wherein the first direction is a direction parallel to the axis of the connector pins.

3. A system according to claim 1 or claim 2 wherein the retaining means comprises a latch mounted to the second module.

4. A system according to claim 1 or claim 2 wherein the retaining means comprises a rail extending along the outer surface of the device housing in the first direction and wherein the second module is provided with a groove engageable with the rail.

5. A system according to claim 4 wherein the retaining means comprises a latch mounted to the second module and wherein a recess is formed in the rail, engageable with the latch.

6. A system according to claim 5, wherein the second module is provided with an aperture and wherein the latch is provided with means for releasing the latch, accessible via the aperture.

7. A system according to claim 6 wherein the releasing means comprises a member affixed to the latch which when the latch is engaged with the rail is in a first position relative to the aperture in the second module and which may be moved by means of a tool inserted into the aperture to a second position to disengage the latch.

8. A system according to claim 5 wherein the latch comprises a rotatable member having projections which are rotatable into engagement with the rail.

9. A system according to claim 8 wherein the latch is provided with a handle which is manually operable to rotate the latch into engagement with the rail.

10. A system according to claim 1 or claim 2 wherein the retaining means comprises a spring clip mounted to the second connector module and clip members mounted to the outer surface of the device housing, engageable with the spring clip.

11. A system according to claim 10 wherein the spring clip and the clip members are conductive, whereby they may be employed to electrically interconnect the device housing to a connector in the second module.

12. A system according to claim 1 or claim 2 wherein the retaining means comprises a latch mounted to one of the first and second modules and a recess is formed in the other of the first and second modules, engageable with the latch.

13. A system according to claim 12, wherein the one of the first and second modules provided with the latch is provided with an aperture and wherein the latch comprises means for releasing the latch, accessible via the aperture.

14. A system according to claim 13 wherein the releasing means comprises a member affixed to the latch which when the latch is engaged is in a first position relative to the aperture and which may be moved by means of a tool inserted into the aperture to a second position to disengage the latch.

15. A kit comprising:

a medical device having a device housing containing electrical circuitry and having a first connector module fixedly mounted to the device housing and having a first set of electrical connectors coupled to the circuitry within the device housing;

a second connector module having a second set of electrical connectors engageable with the first set of connectors and a third set of connectors electrically coupled to the second set of connectors and engageable with the connectors on electrical leads; and means for retaining the second module on an outer surface of the device housing adjacent the first module while the second set of connectors engages the first set of connectors;

wherein the first and second sets of connectors engage one another as a result of movement of the second module in a first direction into engagement with the second connector module and wherein the retaining means comprises means for retaining the second connector module on the outer surface of the device housing during movement of the second module in the first direction; and at least one additional connector module having a fourth set of electrical connectors engageable with the first set of connectors and a fifth set of connectors electrically coupled to the fourth set of connectors and engageable with the connectors on electrical leads; and means for retaining the additional module on the outer surface of the device housing while the fourth set of connectors engages the first set of connectors.

16. A kit, comprising:

a medical device having a device housing containing electrical circuitry and having a first connector module fixedly mounted to the device housing and having a first set of electrical connectors coupled to the circuitry within the device housing;

a second connector module having a second set of electrical connectors engageable with the first set of connectors and a third set of connectors electrically coupled to the second set of connectors and engageable with the connectors on electrical leads; and means for retaining the second module on an outer surface of the device housing adjacent the first module while the second set of connectors engages the first set of connectors;

wherein the first and second sets of connectors engage one another as a result of movement of the second module in a first direction into engagement with the second connector module and wherein the retaining means comprises means for retaining the second connector module on the outer surface of the device housing during movement of the second module in the first direction; and at least one additional connector module having a fourth set of electrical connectors engageable with the first set of connectors and an elongated electrical lead having conductors therein coupled to the fourth set of connectors; and means for retaining the additional module on the outer surface of the device housing while the fourth set of connectors engages the first set of connectors.

* * * * *

UNITED STATES PATENT AND TRADEMARK OFFICE
CERTIFICATE OF CORRECTION

PATENT NO. : 6,006,135
DATED : December 21, 1999
INVENTOR(S) : Kast et al.

It is certified that error appears in the above-identified patent and that said Letters Patent is hereby corrected as shown below:

On the title page, item [75] Inventors: "John E. Kast, Hugo; Andrew J. Ries, Circle Pines, Thomas C. Bischoff, Minneapolis, all of Minn."

should read: --John E. Kast, Hugo; Andrew J. Ries, Circle Pines; Thomas C. Bischoff, Minneapolis, Timothy G. Laske, Shoreveiw; Jeffrey J. Clayton, Ramsey, all of Minn. --.

Signed and Sealed this

Twenty-third Day of January, 2001

Attest:

Q. TODD DICKINSON

*Attesting Officer*    *Commissioner of Patents and Trademarks*